(12) United States Patent
Takada

(10) Patent No.: US 7,987,724 B2
(45) Date of Patent: Aug. 2, 2011

(54) METHOD AND APPARATUS FOR ULTRASONIC CROSS-SECTIONAL INSPECTION

(75) Inventor: Hajime Takada, Chiba (JP)

(73) Assignee: JFE Steel Corporation (JP)

( * ) Notice: Subject to any disclaimer, the term of this patent is extended or adjusted under 35 U.S.C. 154(b) by 339 days.

(21) Appl. No.: 12/158,079

(22) PCT Filed: May 25, 2006

(86) PCT No.: PCT/JP2006/310949
§ 371 (c)(1),
(2), (4) Date: Dec. 17, 2008

(87) PCT Pub. No.: WO2007/072589
PCT Pub. Date: Jun. 28, 2007

(65) Prior Publication Data
US 2009/0241675 A1 Oct. 1, 2009

(30) Foreign Application Priority Data

Dec. 19, 2005 (JP) ................................. 2005-365555

(51) Int. Cl.
*G01N 29/00* (2006.01)
*A61B 8/00* (2006.01)

(52) U.S. Cl. ................ 73/641; 73/597; 73/600; 73/602; 600/447

(58) Field of Classification Search ............... 73/641, 73/597, 598, 602, 626; 600/443, 447; 702/39, 702/66
See application file for complete search history.

(56) References Cited

U.S. PATENT DOCUMENTS

| 3,939,696 A * | 2/1976 | Kossoff ............................ 73/626 |
| 3,974,475 A * | 8/1976 | Burckhardt et al. ............ 367/191 |
| 4,004,454 A * | 1/1977 | Matay .............................. 73/610 |
| 5,381,693 A * | 1/1995 | Kobayashi et al. .............. 73/614 |
| 6,023,660 A | 2/2000 | Dory |
| 6,231,511 B1 * | 5/2001 | Bae ................................ 600/447 |
| 6,405,596 B1 * | 6/2002 | Kruzic ............................ 73/611 |
| 7,581,444 B2 * | 9/2009 | Maurer et al. ................... 73/597 |
| 2009/0114021 A1 * | 5/2009 | den Boer ......................... 73/596 |
| 2010/0024556 A1 * | 2/2010 | Hirose et al. .................... 73/622 |
| 2010/0218609 A1 * | 9/2010 | Reed et al. ...................... 73/598 |

FOREIGN PATENT DOCUMENTS

| JP | 3-248058 | 11/1991 |
| JP | 5-15533 | 1/1993 |
| JP | 6-16086 | 3/1994 |

(Continued)

*Primary Examiner* — Jacques M Saint Surin
(74) *Attorney, Agent, or Firm* — DLA Piper LLP (US)

(57) ABSTRACT

The apparatus and method prevent inspection omission when ultrasonic flaw detection using a transducer array is applied to inspection of a test object being conveyed at a high speed. The method for inspecting a cross section of a test object using a transducer array comprised of many ultrasonic transducers arranged in one dimension includes the steps of transmitting ultrasonic waves from some or all of the ultrasonic transducers in the transducer array, receiving reflected waves generated by the transmitted ultrasonic waves using some or all of the ultrasonic transducers in the transducer array, converting the received signals into digital waveform signals, transforming the timing between the digitalized signal data received by each transducer element in at least one transducer group, which includes plural transducer elements selected from the transducer array, on the basis of the distances between the transducer element and spatially continuous focuses of receiving beam set to be formed in the test object; and summing all the timing-transformed signals received by transducer elements in the transducer group.

11 Claims, 13 Drawing Sheets

FOREIGN PATENT DOCUMENTS

| | | |
|---|---|---|
| JP | 9-133657 | 5/1997 |
| JP | 2671633 | 7/1997 |
| JP | 10-123109 | 5/1998 |
| JP | 2003028846 | 1/2003 |
| JP | 3401199 | 2/2003 |
| SU | 808853 * | 3/1981 |

* cited by examiner

FIG. 12
| SAMPLE | A (SHEET THICKNESS 2.0mm) | B (SHEET THICKNESS 3.0mm) |
|---|---|---|
| APPARATUS OF PRESENT EMBODIMENT | 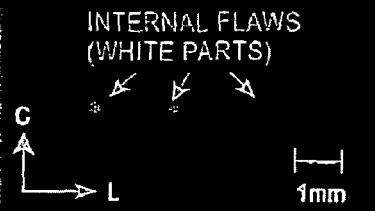 | 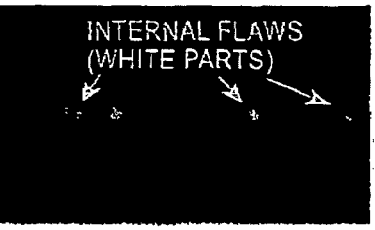 |
| APPARATUS OF PATENT DOCUMENT 2 |  | 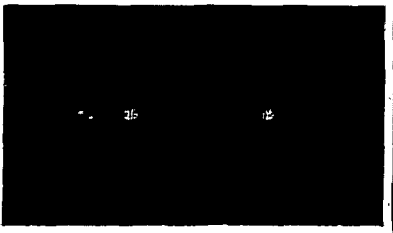 |
| COMMON LINEAR ELECTRONIC SCANNING | 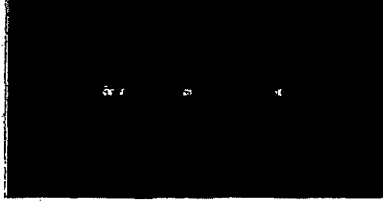 |  | ent
METHOD AND APPARATUS FOR ULTRASONIC CROSS-SECTIONAL INSPECTION

RELATED APPLICATIONS

This is a §371 of International Application No. PCT/JP2006/310949, with an international filing date of May 25, 2006 (WO 2007/072589 A1, published Jun. 28, 2007), which is based on Japanese Patent Application No. 2005-365555, filed Dec. 19, 2005.

TECHNICAL FIELD

This disclosure relates to methods and apparatus for ultrasonic cross-sectional inspection and, more specifically, to methods and apparatus for ultrasonic cross-sectional inspection suitable for use in an ultrasonic inspection apparatus that inspects a test object being carried successively using ultrasonics waves, or ultrasonic inspection apparatus that inspects a test object by scanning an ultrasonic transducer.

BACKGROUND

Industrial products such as metallic materials are often inspected using ultrasonic waves to make sure that there are no harmful defects in them. In recent years, due to reduction in thickness of metallic materials for reduction in weight, changes of manufacturing processes for environmental measures, improvement in internal quality for longer life, and so forth, it has been necessary to detect ultra-minute internal defects of about 20 μm in diameter throughout the length and cross section of a metallic material. To inspect all of the produced metallic material products throughout their lengths and cross sections, it is necessary to inspect products being carried in a production line. The carrying speed of products that require detection of ultra-minute defects is up to about 1000 mm/s. Therefore, it is necessary to detect ultra-minute defects of about 20 μm in diameter throughout the length and cross-section of a product being carried at a high speed of 1000 mm/s. In the case of inspecting a motionless product by scanning an ultra-sonic transducer, it is necessary to scan the ultrasonic transducer at a high speed of 1000 mm/s.

The above-described ultrasonic inspection apparatuses are called ultrasonic flaw detectors. In detecting the above-described internal defects by use of these apparatuses, techniques in which ultrasonic beams are electronically scanned are used for high-speed inspection purpose. One of these techniques, a commonly-used scanning technique called linear electronic scanning, will be described with reference to FIG. 13.

FIG. 13 is a block diagram showing a conventional ultrasonic inspections apparatus. In FIG. 13, reference numeral 101 denotes a transducer array. The transducer array 101 has, at the distal end thereof, many ultrasonic transducers (hereinafter simply referred to as "elements") arrayed at regular intervals. Some of these elements are driven as a group so as to focus an ultrasonic beam on a preset position. In the shown example, the total number of elements is 64 ($101_1$ to $101_{64}$), and the number of elements used as a group is eight. The elements are assigned element numbers 1 to 64. Reference letters $B_1$ to $B_{57}$ denote ultrasonic beams formed using the elements $101_1$ to $101_{64}$. Reference numeral 102 denotes a control circuit that controls transmitting; and receiving of the ultrasonic beams $B_1$ to $B_{57}$.

An outline of transmitting and receiving the ultrasonic beams $B_1$ to $B_{57}$ will be described. First, eight elements $101_1$ to $101_8$ are driven as a group, thereby transmitting and receiving an ultrasonic beam $B_1$ that has a focal point (also called focus) on the center line of the elements $101_1$ to $101_8$. Next, elements $101_2$ to $101_9$ are driven as a group, thereby transmitting and receiving an ultrasonic beam $B_2$ that has a focal point on the center line of the elements $101_2$ to $101_9$. Similarly, elements to be driven are shifted by one element. Finally, elements $101_{57}$ to $101_{64}$ are driven, thereby transmitting and receiving an ultrasonic beam $B_{57}$. In such operation, a test object is electronically scanned with an ultrasonic beam at intervals equal to the element arrangement interval. The control necessary for transmitting and receiving of the above-described focused ultrasonic beams and for electronic scanning is performed by use of the control circuit 102 connected to the transducer array 101.

Focusing of transmitted ultrasonic beams is possible by changing the timing of an electric pulse applied to each element to transmit ultrasonic waves, in the group of elements. Focusing of receiving beams can be achieved by delaying signals received by the group of elements, element by element, by a specific time, and adding them.

It is said that the above-described linear electronic scanning is about 20 times faster than mechanical scanning of an ultrasonic single probe. However, in the case of inspecting a test object carried at a high speed of about 1000 mm/s in a transfer line, for example, of metallic materials using the above-described linear electronic scanning, a significant portion of the test object passes before electronic scanning is completed. Therefore, oversights can occur in inspection.

Publications discussing speeding up the inspection using linear electronic scanning include Japanese Unexamined Patent Application Publication No. 3-248058. Japanese Unexamined Patent Application Publication No. 3-248058 proposes speeding up linear electronic scanning by "an ultrasonic inspection apparatus that scans ultrasonic beams along an array of many ultrasonic transducers, the apparatus including a beam region dividing means that divides all of the ultrasonic beams into a series of beam regions, a beam region selecting means that selects the beam regions in a predetermined order, and a shifting means that sequentially shifts an ultrasonic beam in a selected beam region every time the beam region is selected."

Publications that discuss speeding up the cross-sectional inspection of a test object include Japanese Unexamined Patent Application Publication No. 2003-28846. Japanese Unexamined Patent Application Publication No. 2003-28846 proposes speeding up the cross-sectional inspection of a test object by "an ultrasonic flaw detector including an ultrasonic transducer array having a plurality of transducers that can be arranged along the surface of a test object, an exciting means that excites each transducer of the ultrasonic transducer array with a spike pulse, a waveform memory that stores ultrasonic echoes received by each transducer as waveform data of each transducer, a phase summing means that reads the contents of the waveform memory in which waveform data of each transducer are stored and that makes phase summing of them using a summer, and a focusing means that gives, during reading of the waveform memory, the waveform memory address corresponding to the beam path distance of the dynamic focus set to an arbitrary position within the electronic scanning range."

However, in Japanese Unexamined Patent Application Publication No. 3-248058, the fact remains that scanning of ultrasonic beams is performed by electronic switching, and it is far from a solution to the above-described problem of the oversight in the inspection.

In Japanese Unexamined Patent Application Publication No. 2003-28846, in forming the focuses of the receiving beam by use of all of the received signal data of the transducer array stored in the waveform memory, it is necessary to sequentially shift the focal depth. Therefore, this process disadvantageously takes time. In paragraph [0042] of Japanese Unexamined Patent Application Publication No. 2003-28846 is shown an example in which a cross-sectional inspection ends in 1 ms. However, in the case where the speed of a test object is, for example, 1000 mm/s (60 mpm), the inspection of the test object can only be performed at intervals of 1 mm. If there is a circular planar defect about 100 μm in diameter in the test object, the probability that an ultrasonic beam hits this defect at a right angle is smaller than 1/10.

In Japanese Unexamined Patent Application Publication No. 2003-28846, a focus of a receiving beam is formed at a specific position by phase summing all of the n received signals received by n elements. 200 is taken as an example of n. Since the diameter of a receiving beam at the focal position is inversely proportional to the size of the aperture, a large n might seem to be preferable from the viewpoint of the defect detectability and the resolution. However, each individual ultrasonic transducer (also called "element") constituting the transducer array has a certain width in the array direction, the receiving beam directivity of each individual ultrasonic transducer is limited to a narrow angular range. Assume that, for example, the nominal frequency of the transducer array is 5 MHz, and the element width in the array direction is 0.8 mm (this is a typical element width of a common 5 MHz transducer array). In this case, the angle at which the receive efficiency is within −6 dB in comparison to the receive efficiency on the central receive beam axis (called receive directivity) is about 12° (with respect to the central beam axis). Assume that, using this transducer array and using only elements whose receive directivities with respect to the focus are within −6 dB, a focus is formed at 50 mm from the transducer array. The element located just above the focus is denoted as element i. An element j whose receive directivity with respect to the focus is within −6 dB is located about 11 mm from the element i. Since the element width is 0.8 mm, the element j is the 13th or 14th element from the element i. Therefore, in the above-described case, the total number of elements that mainly contribute to the focus of a receive beam is a little less than 30. As described above, when the technical idea shown in Japanese Unexamined Patent Application Publication No. 2003-28846 is applied to the common case, the phase synthesis of more than 80 percent of the elements is wasted. In addition, in the case where the apparatus shown in Japanese Unexamined Patent Application Publication No. 2003-28846 is applied to the on-line flaw detection in a manufacturing premise, the factory-specific cyclic noise included in the signals received by more than 80 percent of the elements that hardly contribute to formation of a focus increases by addition, and therefore a noise signal of large amplitude tends to be generated. Since a noise signal of large amplitude causes false detection, it is the most detestable problem in the on-line flaw detection.

It could therefore be helpful to prevent inspection omissions when ultrasonic flaw detection using a transducer array is applied to inspect a test object being conveyed at a high speed or when a test object is inspected by moving a transducer array at a high speed. In addition, it could be helpful to provide methods and apparatus free from noise of large amplitude.

SUMMARY

In one aspect, we provide methods for inspecting a cross section of a test object using a transducer array comprised of many ultrasonic transducers arranged in one dimension, comprising: transmitting ultrasonic waves from some or all of the ultrasonic transducers in the transducer array; receiving reflected waves generated by the transmitted ultrasonic waves using some or all of the ultrasonic transducers in the transducer array; converting the received signals into digital waveform signals; transforming the timing between the digitalized signal data received by each transducer element in at least one transducer group, which is comprised of plural transducer elements selected from the transducer array, on the basis of the distances between the transducer elements and spatially continuous focuses of receiving beam set to be formed in the test object; and summing all the time-transformed signals received by transducer elements in the transducer group. The continuous focuses of a receiving beam set to be formed in the test object essentially means a continuous focuses of receiving beam the distance between which is an ultrasonic wave propagation distance corresponding to the sampling time interval of A/D (analog-digital) conversion.

It is preferable that the plural transducer groups comprised of plural transducer elements are selected from the transducer array, and summing is carried out for the plural ultrasonic transducer groups in parallel.

It is preferable that the number of ultrasonic transducer elements constituting each ultrasonic transducer group is changed according to the distance between the transducer array and the focus.

In another aspect, we provide methods for inspecting a cross section of a test object using a transducer array comprised of many ultrasonic transducers arranged in one dimension, comprising: transmitting ultrasonic waves from some or all of the ultrasonic transducers in the transducer array; receiving reflected waves generated by the transmitted ultrasonic waves using some or all in the ultrasonic transducers of the transducer array; converting the received signals into digital waveform signals; extracting, on the basis of the distance between each transducer element in at least one ultrasonic transducer group composed of plural ultrasonic transducer elements selected from the transducer array and n (n≧2) focuses of receiving beam set to be formed in the test object, signals contributing to formation of each of the n focuses from the digitalized received signals by each transducer element; and summing the signals extracted for each of the n focuses.

It is preferable that the plural ultrasonic transducer groups comprised of plural ultrasonic transducer elements are selected from the transducer array, and summing is performed in the ultrasonic transducer groups in parallel.

It is preferable that the number of ultrasonic transducer elements constituting each ultrasonic transducer group is changed according to the distance between the transducer array and the focus.

It is preferable that the distances between the n (n≧2) focuses of receiving beam set to be formed in the test object is changed according to the distance between the transducer array and the focuses.

In still another aspect, we provide apparatus for inspecting a cross section of a test object using a transducer array comprised of many ultrasonic transducers arranged in one dimension, comprising: means for transmitting ultrasonic waves from some or all of the ultrasonic transducers in the transducer array; means for receiving reflected waves generated by the transmitted ultrasonic waves using some or all of the ultrasonic transducers in the transducer array; means for converting the received signals into digital waveform signals; means for transforming the timing between the digitalized signal data received by each transducer in at least one transducer group, which is comprised of plural transducer elements selected from the transducer array, on the basis of the distances between the transducer element and spatially continuous focuses of receiving beam set to be formed in the test object; and means for summing all the timing-transformed signals received by transducer elements in the transducer group.

In yet another aspect, we provide apparatus for inspecting a cross section of a test object using a transducer array comprised of many ultrasonic transducers arranged in one dimension, comprising: means for transmitting ultrasonic waves from some or all of the ultrasonic transducers in the transducer array; means for receiving reflected waves generated by the transmitted ultrasonic waves using some or all of the ultrasonic transducers in the transducer array; means for converting the received signals into digital waveform signals; means for extracting, on the basis of the distance between each transducer element in at least one ultrasonic transducer group comprised of plural of ultrasonic transducers selected from the transducer array and n (n≧2) focuses of receiving beam set to be formed in the test object, signals contributing to formation of each of the n focuses from the digitalized received signals by each transducer element; and means for summing the signals extracted for each of the n focuses.

It is preferable that the means for summing carries out the summing for plural ultrasonic transducer groups in parallel. The term "in parallel" appearing in "carries out the summing . . . in parallel" means the time period from when next transmitting and receiving of ultrasonic waves are performed until when time-axis converted received signals or signals extracted for each of the n focuses are switched to signals obtained by the next transmitting and receiving of ultrasonic waves.

BRIEF DESCRIPTION OF THE DRAWINGS

FIG. 12 is a comparative diagram showing C-scopes obtained using the apparatus of the second structure, Japanese Unexamined Patent Application Publication No. 2003-28846, and a conventional linear electronic scanning.

Figure 1:
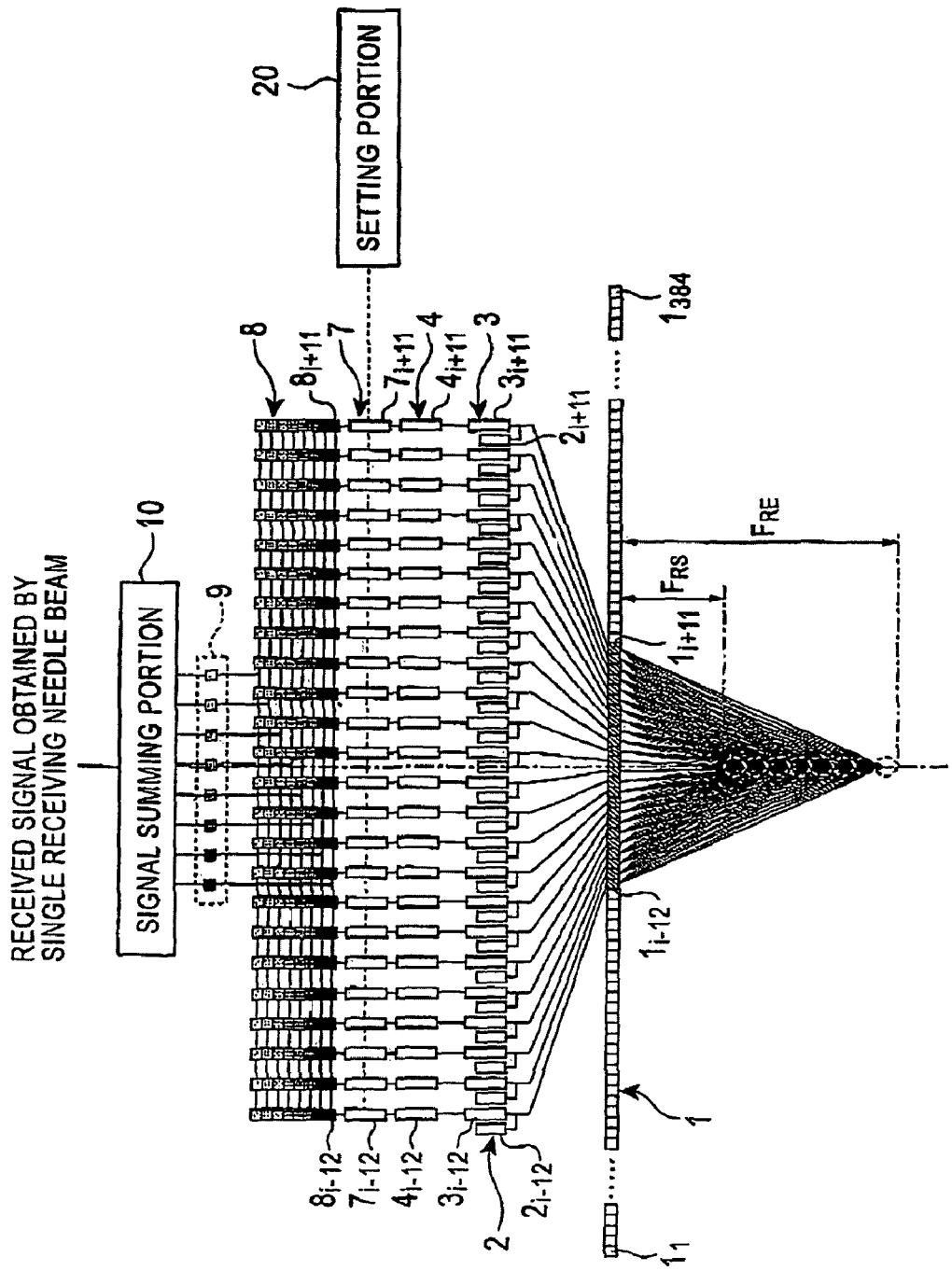
FIG. 1 is a block diagram showing a simplified constitution of a first structure of an ultrasonic inspection apparatus.

The meanings of reference numerals in the figures are as follows:
1 transducer array
$1_1$ to $1_{384}$ ultrasonic transducers
$2_1$ to $2_{384}$ pulsers
$3_1$ to $3_{384}$ receive amplifiers
$4_1$ to $4_{384}$ A/D converters
$7_1$ to $7_{384}$ signal extraction portions
$8_1$ to $8_{384}$ waveform memories
$9_1$ to $9_{384}$ signal summing portions
$10_1$ to $10_{384}$ signal summing portions
$11_1$ to $11_{384}$ time axis conversion portions
$12_1$ to $12_{384}$ waveform memories
$13_1$ to $13_{384}$ signal summing portions
$14_1$ to $14_{384}$ partly clearing portions.

DETAILED DESCRIPTION

Selected, representative examples of our apparatus and methods will hereinafter be described in detail with reference to the drawings.

Figure 2:
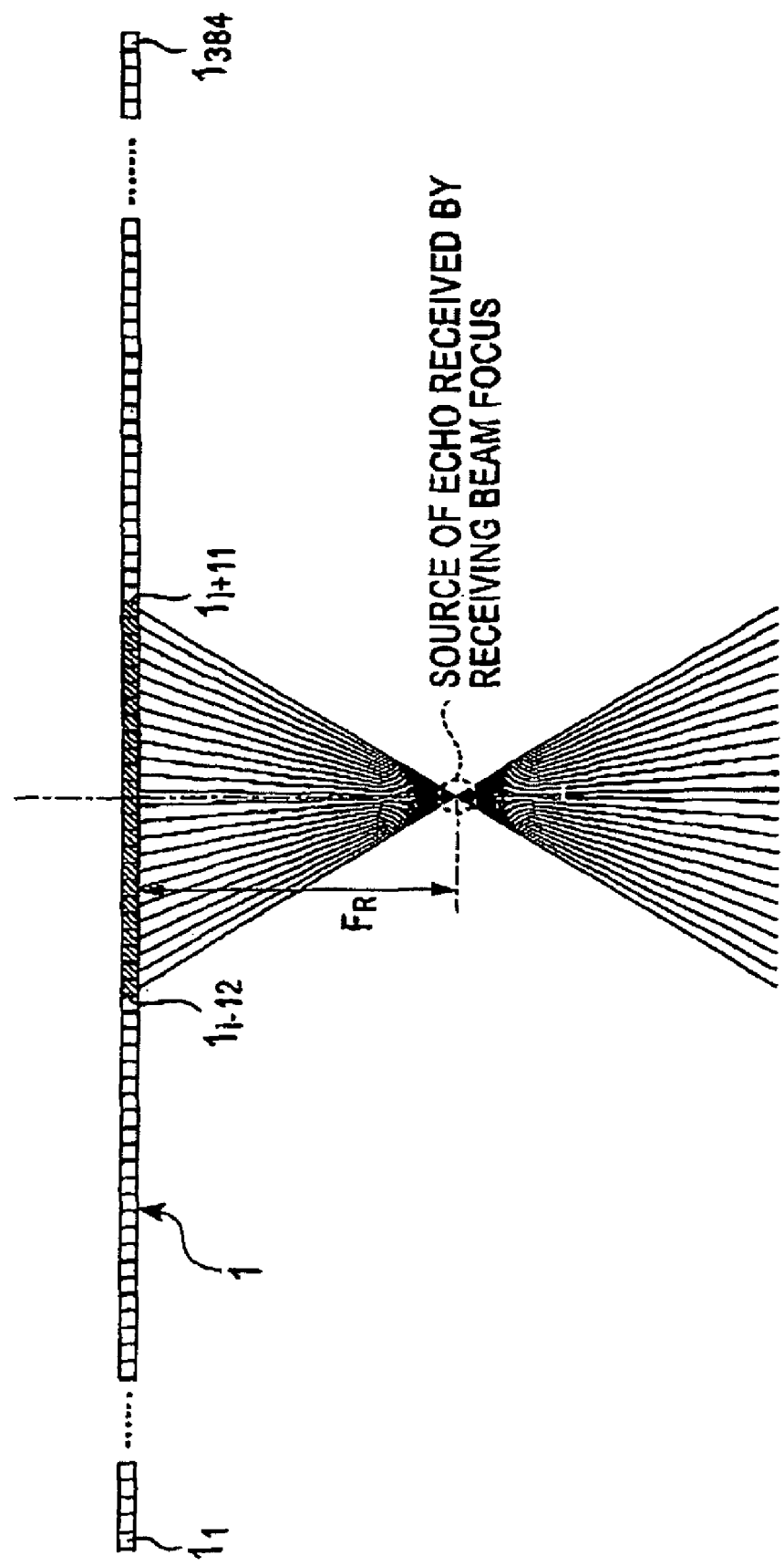
FIG. 2 is an explanatory diagram showing the concept of the first structure.
Figure 3:
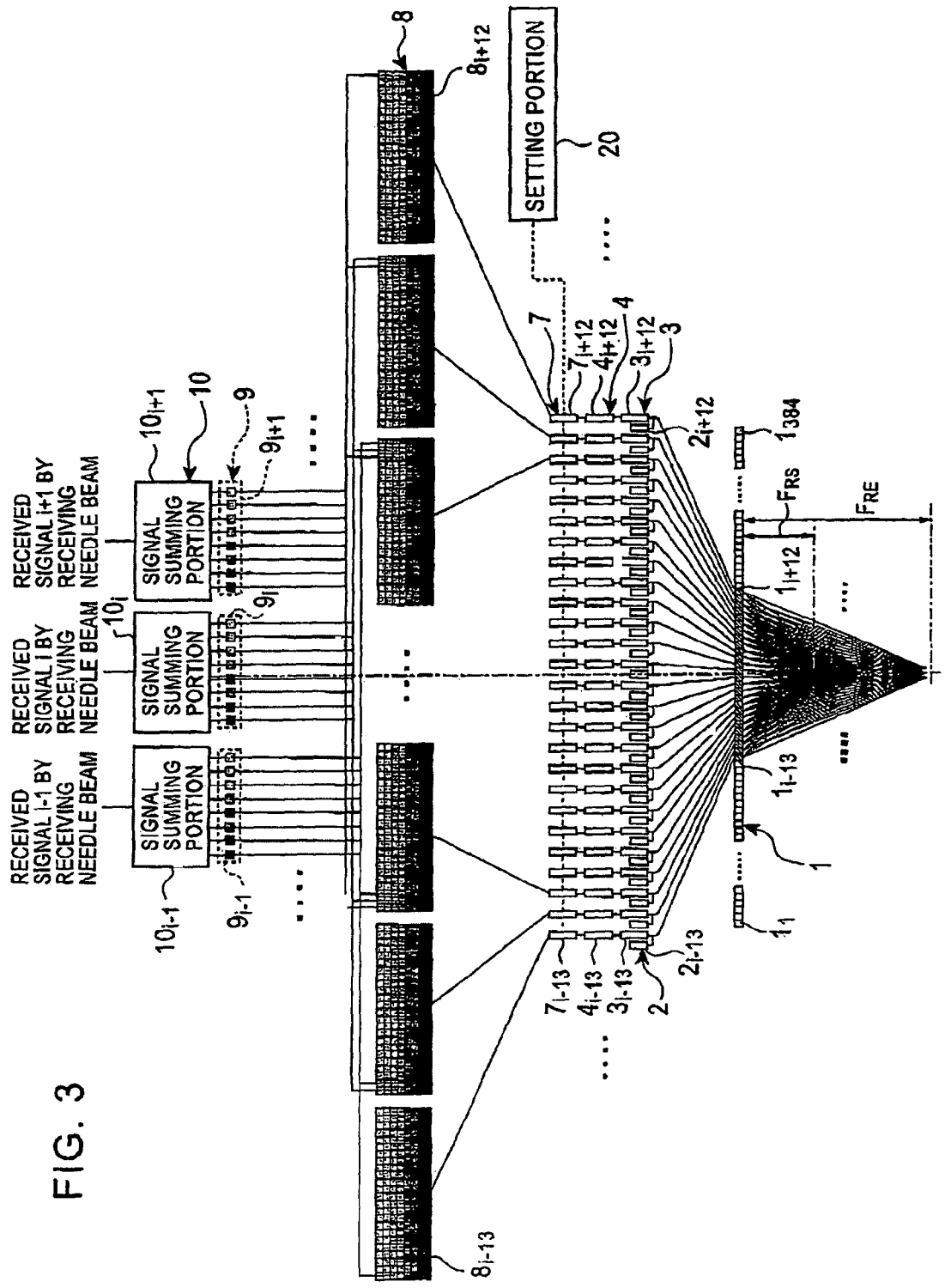
FIG. 3 is a block diagram showing the overall constitution of the first structure.

FIG. 1 is a block diagram showing a simplified example of a first structure of an ultrasonic inspection apparatus. FIG. 2 is an explanatory diagram showing the point of the first structure. FIG. 3 is a block diagram showing the whole of the first structure.

As the first structure, a case will be described where the total number of elements (ultrasonic transducers) is 384, and the number of elements constituting a group used for forming a receive converging beam is 24. In this structure, a receive beam having a small beam diameter (hereinafter referred to as needle beam) is formed using 24 elements under an array thereof. In addition, a receive needle beam is formed under an array of 24 elements that can be selected from 384 elements at the same time, and thereby a receive needle beam curtain of closely arranged receive needle beams is formed under a transducer array 1. In the first structure, to form the receive needle beam, a beam converges and forms focuses at eight (n=8) positions different in the distance from the transducer array. Signals only of proximities of the focuses (predetermined regions around the beam focus positions) are extracted from the signals received by the elements. By additively synthesizing them, wave receiving by the receive needle beam is achieved.

As shown in FIG. 1 (simplified diagram) and FIG. 3 (overall diagram), the first structure includes a transducer array 1, pulsers $2_1$ to $2_{384}$ that apply electric pulses to elements $1_1$ to $1_{384}$ to transmit ultrasonic waves from elements $1_1$ to $1_{384}$ of the transducer array 1, receive amplifiers $3_1$ to $3_{384}$ for amplifying ultrasonic signal received by the elements $1_1$ to $1_{384}$, A/D converters $4_1$ to $4_{384}$ that convert the receive ultrasonic signals after amplification into digital signals, signal extraction portions $7_1$ to $7_{384}$ that extract only receive signals of the receive beam focus from the digitalized receive signals, waveform memories $8_1$ to $8_{384}$ that store the extracted signals, and an SIGNAL SUMMING PORTION 9 that additively synthesizes the extracted signals to generate a receive synthesized signal equivalent to a signal received using a receive beam converging at a point (also called "receive beam focus"), and a SIGNAL SUMMING PORTION 10 that temporally joins signals from the SIGNAL SUMMING PORTION 9 and thereby generates a receive signal equivalent to a signal received using a receive beam formed under a position between transducers $1_i$ and $1_{i+1}$. That is, in this structure, elements of the transducer array $1_1$ to $1_{384}$ are provided with pulsers $2_1$ to $2_{384}$, receive amplifiers $3_1$ to $3_{384}$, A/D converters $4_1$ to $4_{384}$, signal extraction portions $7_1$ to $7_{384}$, and waveform memories $8_1$ to $8_{384}$, respectively. Some of the pulsers $2_1$ to $2_{384}$, receive amplifiers $3_1$ to $3_{384}$, A/D converters $4_1$ to $4_{384}$, signal extraction portions $7_1$ to $7_{384}$, waveform memories $8_1$ to $8_{384}$, signal summing portions $9_1$ to $9_{384}$, and signal summing portions $10_1$ to $10_{384}$ that are not used for description of the operation are omitted from the figures. Components that are not used for description of operation are omitted also from the other figures.

FIG. 2 shows the concept of formation of a receive needle beam in the first structure. Ultrasonic waves are transmitted from all of the elements $1_1$ to $1_{384}$ of the transducer array 1. Ultrasonic reflected signals (echoes) from a test object are received using all of the elements $1_1$ to $1_{384}$ of the transducer array 1. The ultrasonic signals received by the elements $1_1$ to $1_{384}$ are amplified by the receive amplifiers $3_1$ to $3_{384}$ shown in FIG. 1 and are thereafter converted into digital signals by the A/D converters $4_1$ to $4_{384}$. By performing phase focusing of these digitalized signals and thereafter performing additive synthesis, a receive converging beam such as that shown in FIG. 2 can be formed. In this structure, it is noted that only the reflected signals from the region shown by a dashed circle in FIG. 2 are extracted to inspect a cross section of a test object with a high resolution. Specifically, only the signals received within the time range corresponding to the distances between the elements $1_{i-12}$ to $1_{i+11}$ and the circular region are extracted using the signal extraction portions $7_1$ to $7_{384}$ from the received digital signals converted by the A/D converters $4_1$ to $4_{384}$, and then additive synthesis is performed. The extraction condition parameters of the signal extraction portion 7 are set on the basis of information such as the distances between the elements $1_{i-12}$ to $1_{i+11}$ and the circular region input from the setting portion 20, and the speed of sound in the medium. A plurality of the region shown by a dashed circle are set on the dashed-dotted line in FIG. 2 so that circular regions such as those shown in FIG. 1 are arranged in a seamless manner (a plurality of focal lengths $F_R$ are set so that the regions are arranged in a seamless manner). Next, only the signals received from these regions are extracted and additively synthesized. In this way, signals only from the proximity of the dashed-dotted line can be received. At this time, the receive beam formed can be said to be a needle beam localized in a narrow region corresponding to the diameter of a converging beam centered on the dashed-dotted line.

FIG. 1 shows a simplified constitution in which is formed a single receive needle beam localized in the narrow region centered on the dashed-dotted line. Eight regions (circular regions shown by solid line) at which a receive needle beam converges are set so that a receive needle beam can be formed at distance $F_{RS}$ to $F_{RE}$ from the elements $1_{i-12}$ to $1_{i+11}$ of the transducer array. The specific operation is as follows. Ultrasonic waves are transmitted from all of the elements $1_1$ to $1_{384}$ of the transducer array 1. Ultrasonic reflected signals (echoes) from the test object are received using all of the elements $1_1$ to $1_{384}$ of the transducer array 1. The ultrasonic signals received by the elements $1_{i-12}$ to $1_{i+11}$ are amplified by the receive amplifier $3_{i-12}$ to $3_{i+11}$ and are thereafter converted into digital signals by the A/D converters $4_{i-12}$ to $4_{i+11}$. To form a receive beam converged at the centers of the eight regions, the signal extraction portions $7_{i-12}$ to $7_{i+11}$ extract signals received from the regions and send them to the waveform memories $8_{i-12}$ to $8_{i+11}$. The waveform memories $8_{i-12}$ to $8_{i+11}$ are each divided into eight regions (shown using eight kinds of patterns in FIG. 1) and store signals received from the eight regions. The signals recorded in the waveform memories $8_{i-12}$ to $8_{i+11}$, are sent to the SIGNAL SUMMING PORTION 9 and are additively synthesized. In FIG. 1, waveform memories of the same pattern are connected to a region of the same pattern of the SIGNAL SUMMING PORTION 9 using a single line. This shows that signals received from the same region are guided to the SIGNAL SUMMING PORTION 9. Additive synthesis may be performed after weighting the signals stored in the waveform memories $8_{i-12}$ to $8_{i+11}$ according to the positional relationship between the element $1_{i-12}$ to $1_{i+11}$ and the focus. Signals of receive beams converging at the eight regions thus obtained by additive synthesis are sent to the SIGNAL SUMMING PORTION 10 and are combined into a single received signal.

Figure 4:
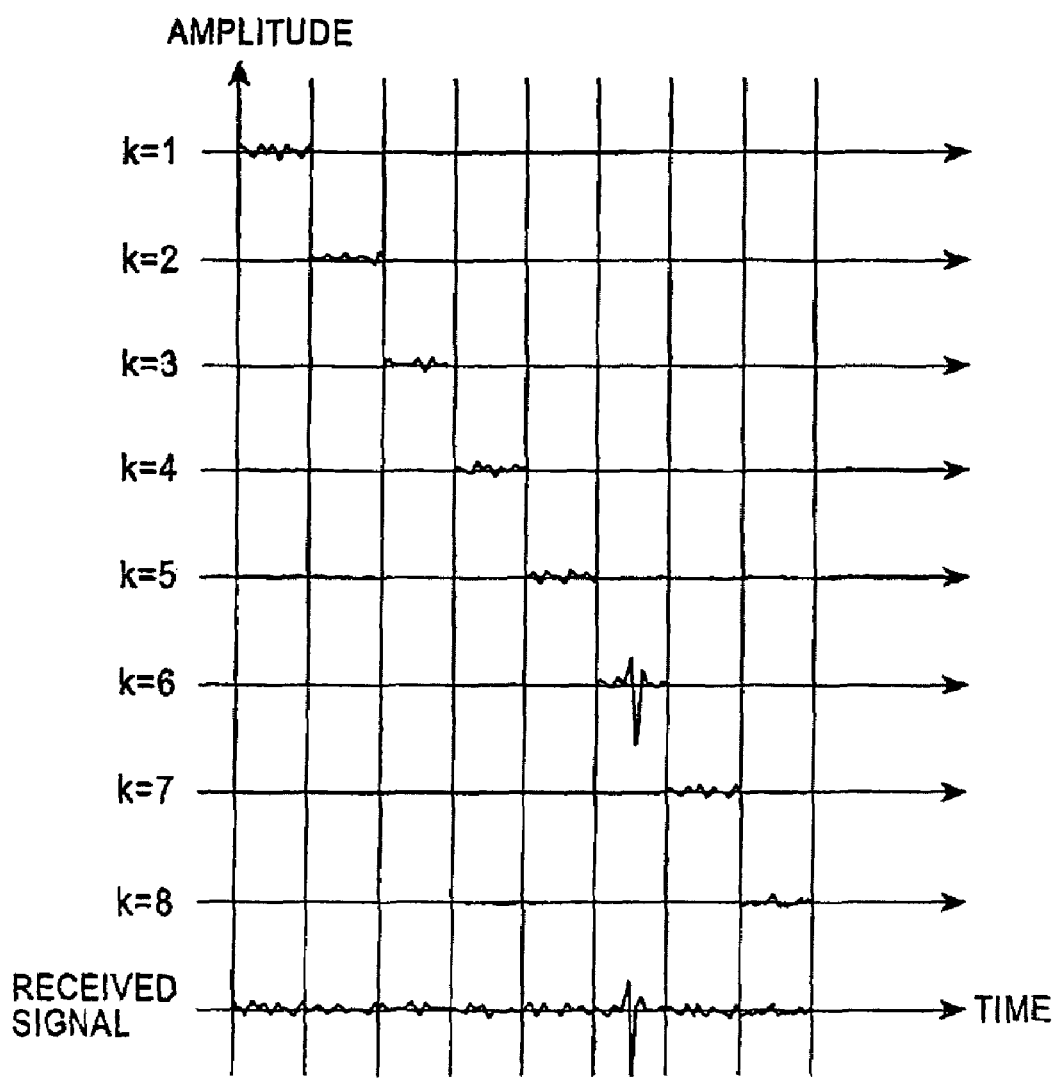
FIG. 4 is an explanatory diagram showing the operation of the SIGNAL SUMMING PORTION.

Next, operation of the SIGNAL SUMMING PORTION 10 will be described with reference to FIG. 4. The eight regions are denoted by region k (k=1, 2, 3, . . . , 8). The signal obtained from the receive beam converging at the region k has a time width corresponding to the size of the extracted region as shown, for example, in k=1 to k=8 of FIG. 4. Since the distances between the transducer array 1 and each region are different, signals received by the transducer array 1 from each region appear at different times. The SIGNAL SUMMING PORTION 10 adds these signals, thereby generating a single receive signal. In this way, a signal received by a receive needle beam formed between the distances $F_{RS}$ and $F_{RE}$ is obtained.

FIG. 3 shows a constitution in which receive needle beams are arranged at the same time under elements of a transducer array 1 and thereby a receive needle beam curtain is formed. In this constitution, a total of 361 receive needle beams are formed under elements $1_j$ to $1_{j+1}$ (j=12, 13, 14, . . . , 370, 371, 372) of the transducer array 1. In FIG. 3, to avoid complicating the figure, a receive needle beam is formed under each of three positions: elements $1_{i-13}$ to $1_{i+10}$, elements $1_{i-12}$ to $1_{i+11}$, and elements $1_{i-11}$ to $1_{i+12}$. The receive needle beam formed by the elements should be denoted $1_{i-13}$ to $1_{i+10}$, the receive needle beam formed by the elements $1_{i-12}$ to $1_{i+11}$, and the receive needle beam formed by the elements $1_{i-11}$ to $1_{i+12}$ by $NB_{i+1}$, $NB_i$, and $NB_{i+1}$, respectively. The operations of the transducer array 1, the pulser 2, the receive amplifier 3, and the A/D converter 4 are the same as those described with reference to FIG. 1. Since one element of the transducer array is used for forming 24 receive needle beams at 24 positions at the same time, it is necessary to store signals from proximities of a total of 24×8 receive beam focuses in a waveform memory connected to each element. Therefore, the waveform memories $8_1$ to $8_{384}$ are each divided into 24×8 regions. The signal extraction portion 7 that sends out received signals to the waveform memory 8 extracts 24×8 signals from received signals according to the distances between each element and the 24×8 regions at which receive beams are converged, and sends them to the waveform memory 8. To obtain received signals, for example, of receive needle beam $NB_{i-1}$ from the received signals recorded in the waveform memory 8, signals from the proximities of the eight receive beam focuses (predetermined regions based on the focal positions) set under the elements $1_{i-13}$ to $1_{i+10}$ (specifically, under a position between element $1_{i-2}$ and element $1_{i-1}$) are sent to the SIGNAL SUMMING PORTION 9, out of the received signals recorded in the waveform memories $8_{i-13}$ to $8_{i+10}$. These signals are additively synthesized in the SIGNAL SUMMING PORTION 9. Signals thus obtained from receive beams converging at the eight regions are sent to the SIGNAL SUMMING PORTION 10 and are combined into a single received signal. In this way, a signal received using the receive needle beam $NB_{i-1}$ formed between distances $F_{RS}$ and $F_{RE}$ is obtained. Signals received using other receive needle beams can also be obtained using the same process.

In this structure, to avoid complicating the explanation, wave receiving is performed using the receive needle beam in a single medium. In the case where there are two kinds of media such as the case of immersion flaw detection of a metallic material, the refraction of ultrasonic waves is considered in calculation of the distances.

The structure shows a method in which eight receive beam focuses are set under 24 elements and a receive needle beam is formed. This is illustrative only. Any number of elements can be used for forming a beam as long as the number is four or more. The number of receive beam focuses can also be changed according to the thickness of the test object and necessary resolution and detectability.

In this structure, focuses of a receive beam are set at substantially regular intervals. This is also illustrative only. Focuses of a receive beam can be set at irregular intervals. Since the convergence range of a receive beam in the transmitting direction increases with the distance between the focus and the transducer array, the distance between receive beam focuses can be determined accordingly.

The diameter $B_d$ of an ultrasonic beam at the focal position can be roughly expressed by the following equation (1):

$$B_d = \lambda \cdot F/D \tag{1}$$

$\lambda$: wavelength of ultrasonic wave
F: focal length of converging beam
D: width of group of transducers (corresponding to element pitch×number of elements).

Therefore, increasing the focal length F with the transducer width D constant increases the beam diameter $B_d$. Therefore, D can be changed so that a beam has a desired diameter according to the focal length F. Specifically, according to the focal length F, the number of elements used for forming a receive needle beam can be changed.

Next, a second structure will be described in detail with reference to the drawings.

Figure 5:
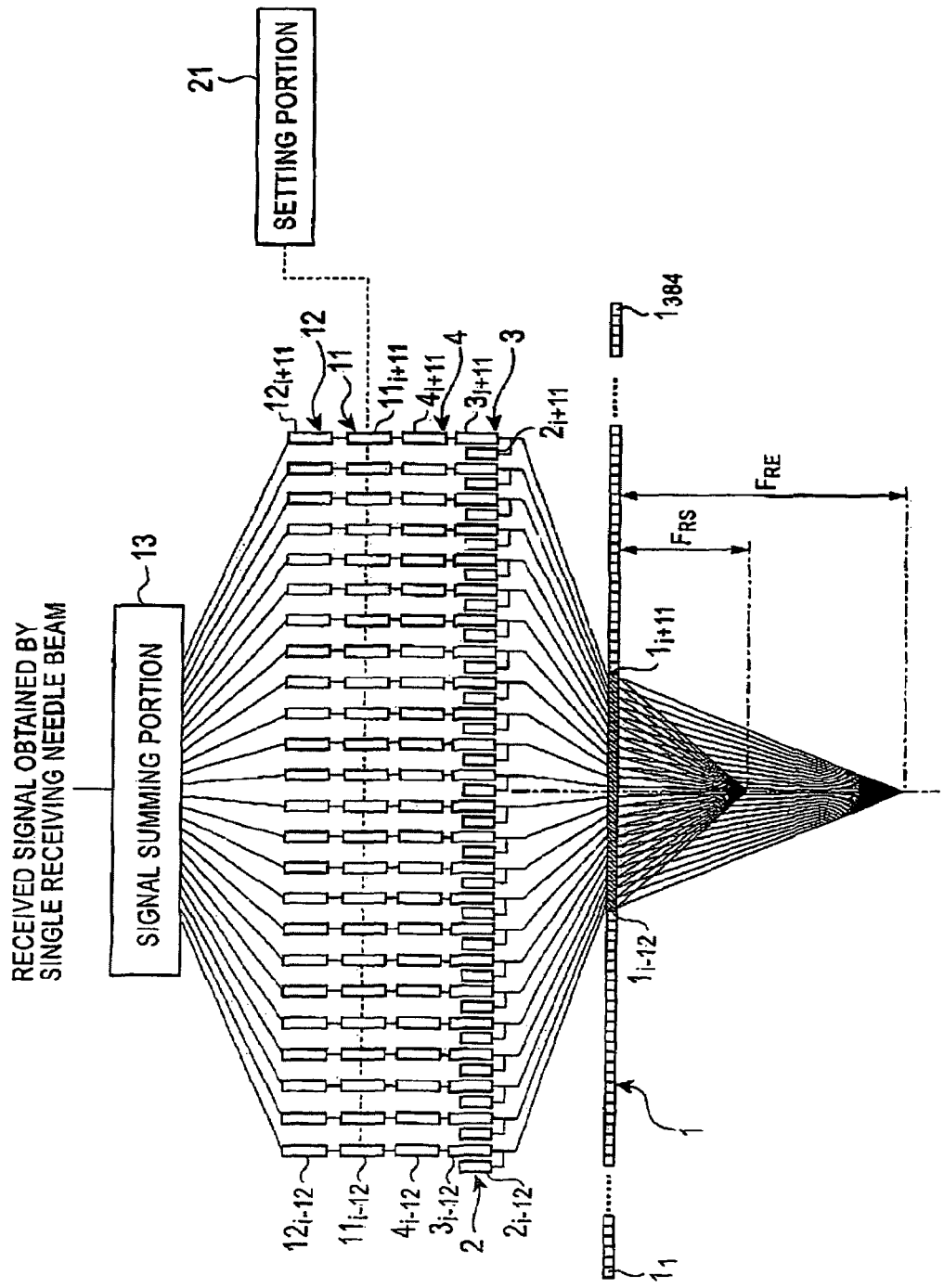
FIG. 5 is a block diagram showing a simplified constitution of a second structure of an ultrasonic inspection apparatus.
Figure 6:
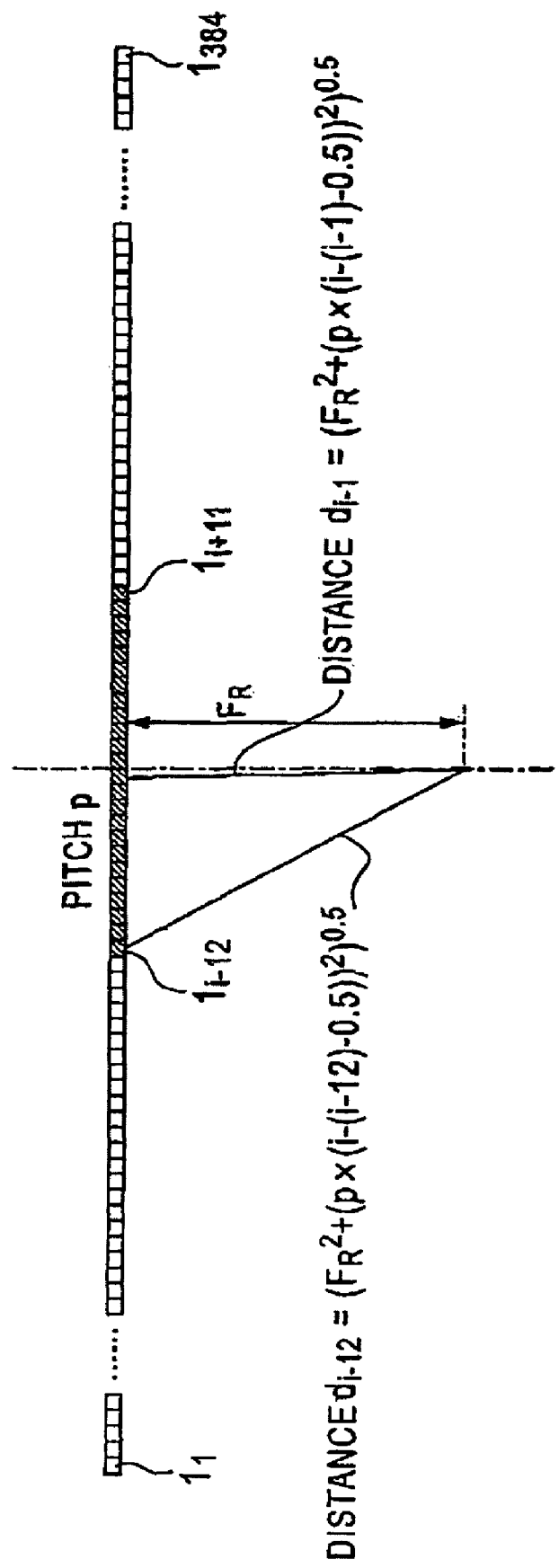
FIG. 6 is an explanatory diagram showing the concept of the second structure.
Figure 7:
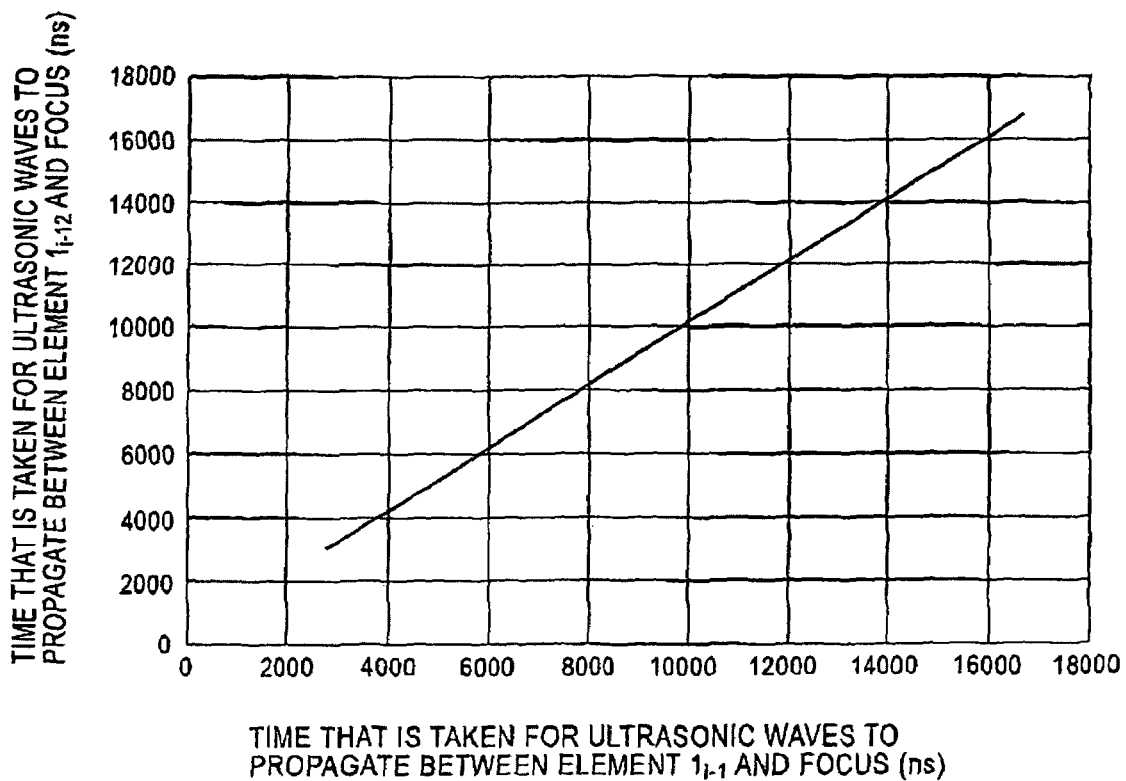
FIG. 7 is an explanatory diagram showing the relationship between the times ultrasonic waves take to propagate between two specific elements and a focus in the second structure.
Figure 8:
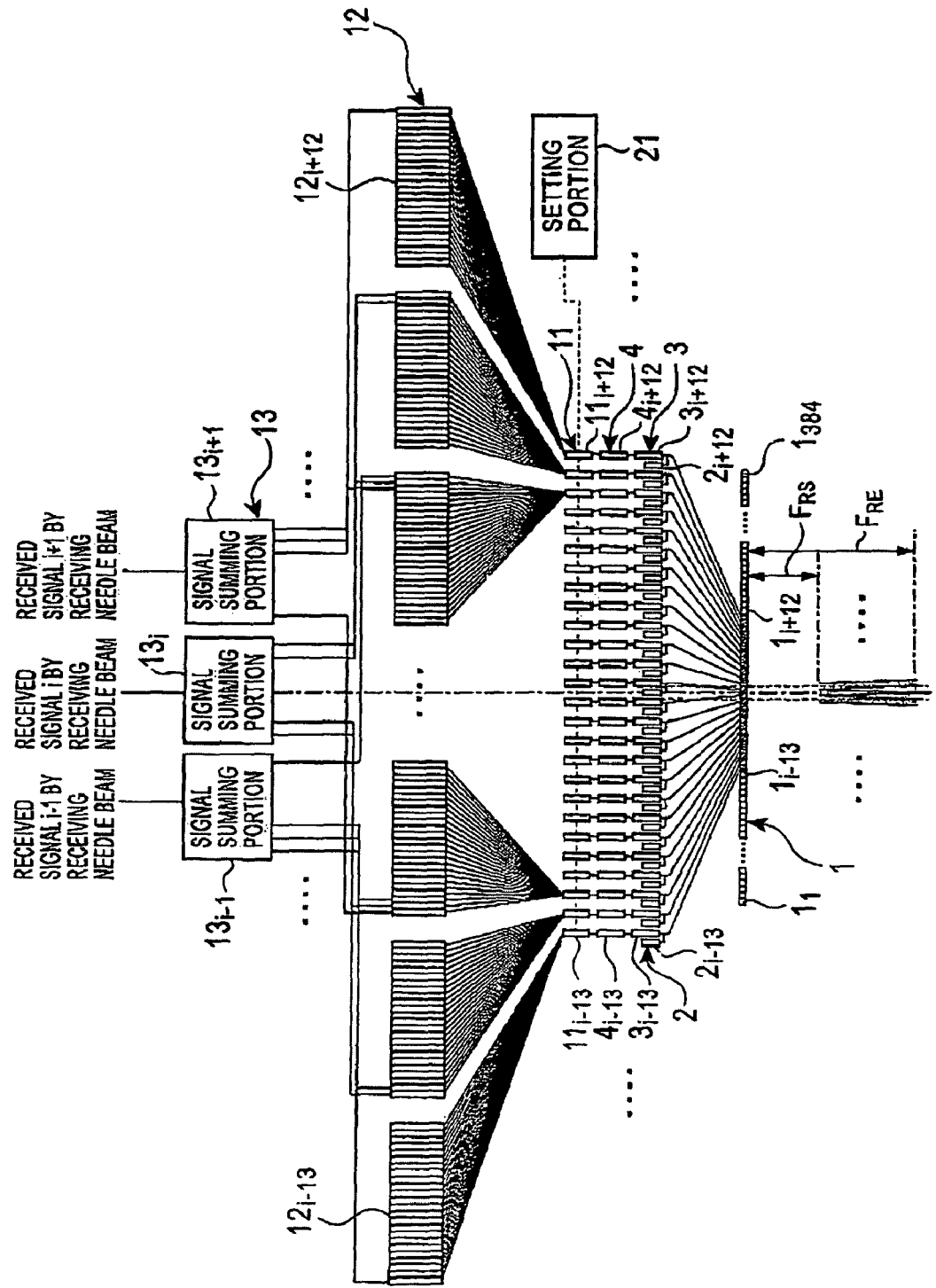
FIG. 8 is a block diagram showing the overall constitution of the second structure.

FIG. 5 is a block diagram showing a simplified example of the second structure. FIG. 6 is an explanatory diagram showing the point of the second structure. FIG. 7 is an explanatory diagram showing the relationship between the times ultrasonic waves take to propagate between two specific elements and a focus. FIG. 8 is a block diagram showing the whole of the second structure.

As the second structure, a case will be described where the total number of elements is 384, and the number of elements constituting a group used for forming a receive converging beam is 24. In this structure, a thin receive beam (hereinafter referred to as needle beam) including a continuous line of focuses is formed using 24 elements under the center in the array direction thereof. In addition, a receive needle beam is formed under an array of 24 elements that can be selected from 384 elements at the same time, and thereby a receive needle beam curtain of closely-arranged receive needle beams is formed under a transducer array 1. In this structure, a continuous line of focuses of a receive converging beam is formed using 24 elements.

As shown in FIG. 5 (simplified diagram) and FIG. 8 (overall diagram), this structure includes a transducer array 1, pulsers $2_1$ to $2_{384}$ that apply electric pulses to elements $1_1$ to $1_{384}$ to transmit ultrasonic waves from elements $1_1$ to $1_{384}$ of the transducer array 1, receive amplifiers $3_1$ to $3_{384}$ for amplifying ultrasonic signal received by the elements $1_1$ to $1_{384}$, A/D converters $4_1$ to $4_{384}$ that convert the receive ultrasonic signals after amplification into digital signals, time axis conversion portions $11_1$ to $11_{384}$ that convert the time axes of digitalized received signals, waveform memories $12_1$ to $12_{384}$ that store the time-axis converted signals, and an SIGNAL SUMMING PORTION 13 that generates a received signal equivalent to a signal received using a needle beam including a continuous line of focuses and formed just under a position between transducers $1_i$ and $11_{i+1}$, using the stored time-axis converted signals. That is, in this structure, elements of the transducer array $1_1$ to $1_{384}$ are provided with pulsers $2_1$ to $2_{384}$, receive amplifiers $3_1$ to $3_{384}$, A/D converters $4_1$ to $4_{384}$, time axis conversion portions $11_1$ to $11_{384}$, and waveform memories $12_1$ to $12_{384}$, respectively.

FIG. 6 shows the concept of formation of a receive needle beam in this structure. Ultrasonic waves are transmitted from all of the elements $1_1$ to $1_{384}$ of the transducer array 1. Ultrasonic reflected signals (echoes) from a test object are received using all of the elements $1_1$ to $1_{384}$ of the transducer array 1. The ultrasonics signals received by the elements $1_1$ to $1_{384}$ are amplified by the receive amplifiers $3_1$ to $3_{384}$ shown in FIG. 5 and are thereafter converted into digital signals by the A/D converters $4_1$ to $4_{384}$. By performing phase focusing of these digitalized signals and thereafter performing additive synthesis, a receive converging beam such as that shown in FIG. 5 can be formed.

In this structure, it is noted that, as shown in FIG. 6, in the case where a receive beam focus is formed under the elements $1_{i-12}$ to $1_{i+11}$ and at a position of a distance $F_R$ from the transducer array 1, the distance between the elements $1_{i-12}$ to $1_{i+11}$ and the focal position is expressed by a monotonic increasing function of the distance $F_R$. In the example shown in FIG. 6, since a focus is set under the intermediate point between $1_{i-1}$ and $1_i$, the elements nearest to the focus are $1_{i-1}$ and $1_i$. FIG. 7 contrastively shows the time ultrasonic waves take to propagate between the element and the focus, and the time ultrasonic waves take to propagate between the element $1_{i-12}$, which is the farthest from the focus, and the focus. In this calculation, the speed of ultrasonic waves in the medium through which ultrasonic waves propagate is 1500 m/s, the element pitch p is 0.2 mm, and $F_R$ is changed from 4 mm to 25 mm.

As shown in FIG. 7, there is a relationship of a monotonically changing function (hereinafter referred to as propagation time relationship) between the times ultrasonic waves take to propagate between the two elements and the focus. In FIG. 7, the horizontal axis represents propagation time converted from the distance $d_{i-1}$ of FIG. 6, and the vertical axis represents propagation time converted from the distance $d_{i-12}$ of FIG. 6. Therefore, by adjusting the time axis of the signal received by one element (the time the signal is received) to the time axis of the signal received by the other element (the time the signal is received) using the relationship shown in FIG. 7 (hereinafter referred to as "time axis conversion"), the phases of the two can always be adjusted to each other even if the distance $F_R$ between the focus and the transducer array 1 changes.

There is the same relationship as that shown in FIG. 7 between the time ultrasonic waves take to propagate between the element $1_{i-1}$ and the focus and the time ultrasonic waves take to propagate between an element other than the element $1_{i-12}$ and the focus. Therefore, by beforehand calculating these relationships and converting the time axes of received signals, the phase of an element other than the element $1_{i-12}$ and the phase of the element $1_{i-1}$ can also be adjusted to each other regardless of the distance $F_R$ between the focus and the transducer array 1. That is, by converting the time axes of signals received by elements $1_{i-12}$ to $1_{i+11}$, a thin receive beam including a continuous line of focuses can be formed under the elements $1_{i-12}$ to $1_{i-11}$. This receive beam can be said to be a needle beam localized in a narrow region centered on the dashed-dotted line.

Although, in the above description, the fiducial element for time axis conversion is the element $1_{i-1}$, the fiducial element can be any of the 24 elements. However, when time axis conversion is performed by reference to the element nearest to the focus, the number of data after time axis conversion can be minimized (the time ultrasonic waves take to propagate between the element and the focus is shortest), and therefore this is advantageous for manufacturing the apparatus.

More specifically, the time axis conversion is performed as follows. Assume that the fiducial element for time axis conversion is the element $1_{i-1}$. Let this time axis be denoted as t. The time axis to $t_{i-12}$ of the element whose time axis is converted (for example, element $1_{i-12}$) can be expressed, by reference to FIG. 7, using a function, as $t_{i-12}=f_{i-12}(t)$. The amplitude of the signal received by the element $1_{i-12}$ is expressed, using a function A, as $A_{i-12}(t_{i-12})$. Therefore, the operation of time axis conversion is to obtain $A_{i-12}(t)$ and can also be expressed, using an inverse function, as $A_{i-12}(f^1_{i-12}(t_{i-12}))$. The time axis conversion portion is beforehand provided with a time axis conversion relationship necessary for this operation from the setting portion 21. Signals handled here are digital data. The number of data of the element nearest to the focus is the smallest (the propagation distance of ultrasonic waves is short). Therefore, when the element nearest to the focus is used as the fiducial, the number of data is reduced in the time axis conversion of other elements. To reduce the number of data, a filtering operation designed so that data of large amplitude are not lost can be used.

FIG. 5 shows a simplified constitution in which is formed a single receive needle beam localized in a narrow region corresponding to the convergence size of a beam centered on the dashed-dotted line. A time axis conversion portion 11 that performs time axis conversion of received and A/D converted signals is provided so that a receive needle beam including a continuous line of focuses can be formed under the elements $1_{i-12}$ to $1_{i+11}$ of the transducer array and between distances $F_{RS}$ and $F_{RE}$.

The specific operation is as follows. Ultrasonic waves are transmitted from all of the elements $1_1$ to $1_{384}$ of the transducer array 1. Ultrasonic reflected signals (echoes) from the test object are received using all of the elements $1_1$ to $1_{384}$ of the transducer array 1. The ultrasonic signals received by the elements $1_{i-12}$ to $1_{i+11}$ are amplified by the receive amplifier $3_{i-12}$ to $1_{i+11}$ and are thereafter converted into digital signals by the A/D converters $4_{i-12}$ to $4_{i+11}$. The time axis conversion portions $11_{i-12}$ to $11_{i+11}$ input beforehand calculated and stored time axis conversion-related data into the setting portion 21 so that a continuous line of focuses is set between distances $F_{RS}$ and $F_{RE}$. On the basis thereof, the time axis conversion portions $11_{i-12}$ to $11_{i+11}$ converts the time axes of signals received by elements other than the fiducial element and sends them to the waveform memories $12_{i-12}$ to $12_{i+11}$. Signals of the fiducial element are sent as they are. The signals recorded in the waveform memories $12_{i-12}$ to $12_{i+11}$ are sent to the SIGNAL SUMMING PORTION 13 and are additively synthesized. In this way, a signal received using a receive needle beam formed between the distances $F_{RS}$ and $F_{RE}$ is obtained.

FIG. 8 shows a constitution in which receive needle beams are arranged at the same time under elements of a transducer array 1 and thereby a receive needle beam curtain is formed. In this constitution, a total of 361 receive needle beams are formed under elements $1_j$ to $1_{j+1}$ (j=12, 13, 14, ..., 370, 371, 372) of the transducer array 1. In FIG. 8, to avoid complicating the figure, a receive needle beam is formed under each of three positions: elements $1_{i-13}$ to $1_{i+10}$, elements. $1_{i-12}$ to $1_{i+11}$, and elements $1_{i-11}$ to $1_{i+12}$. The receive needle beam formed by the elements is denoted as $1_{i-13}$ to $1_{i+10}$, the receive needle beam formed by the elements $1_{i-12}$ to $1_{i+11}$, and the receive needle beam formed by the elements $1_{i-11}$ to $1_{i+12}$ by $NB_{i-1}$, $NB_i$, and $NB_{i+1}$, respectively. The operations of the transducer array 1, the pulser 2, the receive amplifier 3, and the A/D converter 4 are the same as those described with reference to FIG. 5. Since one element of the transducer array is used for forming 24 receive needle beams at the same time, it is necessary to store a total of 24 time-axis converted signals in a waveform memory connected to each element. Therefore, the waveform memories $12_1$ to $12_{384}$ are each divided into 24 regions. The time axis conversion portion 11 that sends out time-axis converted signals to the waveform memory 12 generates 24 time-axis converted signals from signals received, according to the distances between each element and the positions where 24 receive needle beams are formed, and sends them to the waveform memory 12. To obtain received signals, for example, of receive needle beam $NB_{i-1}$ from the received signals recorded in the waveform memory 12, signals time-axis converted so as to form a receive needle beam under the elements $1_{i-13}$ to $1_{i+10}$ (under a position between element $1_{i-2}$ and element $1_{i-1}$) are sent to the SIGNAL SUMMING PORTION $13_{i-1}$, out of the time-axis converted signals recorded in the waveform memories $12_{i-13}$ to $12_{i+10}$. These signals are additively synthesized in the SIGNAL SUMMING PORTION 13. In this way, a signal received using the receive needle beam $NB_{i-1}$ formed between distances $F_{RS}$ and $F_{RE}$ is obtained. Signals received using other receive needle beams can also be obtained using the same process.

In this structure, to avoid complicating the explanation, wave receiving is performed using the receive needle beam in a single medium. In the case where there are two kinds of media such as the case of immersion flaw detection of a metallic material, it goes without saying that refraction of ultrasonic waves is considered in calculation of the distances.

The structure shows a method in which a receive needle beam including a continuous line of focuses is formed under 24 elements. This is illustrative only. Any number of elements can be used for forming a beam as long as the number is four or more.

The diameter $B_d$ of an ultrasonic beam at the focal position can be roughly expressed by the above-mentioned equation (1). Therefore, increasing the focal length F with the transducer width D constant increases the beam diameter $B_d$. Therefore, as in the first structure, D can be changed according to the focal length F. Specifically, according to the focal length F, the number of elements used for forming a receive needle beam can be changed.

Figure 9:
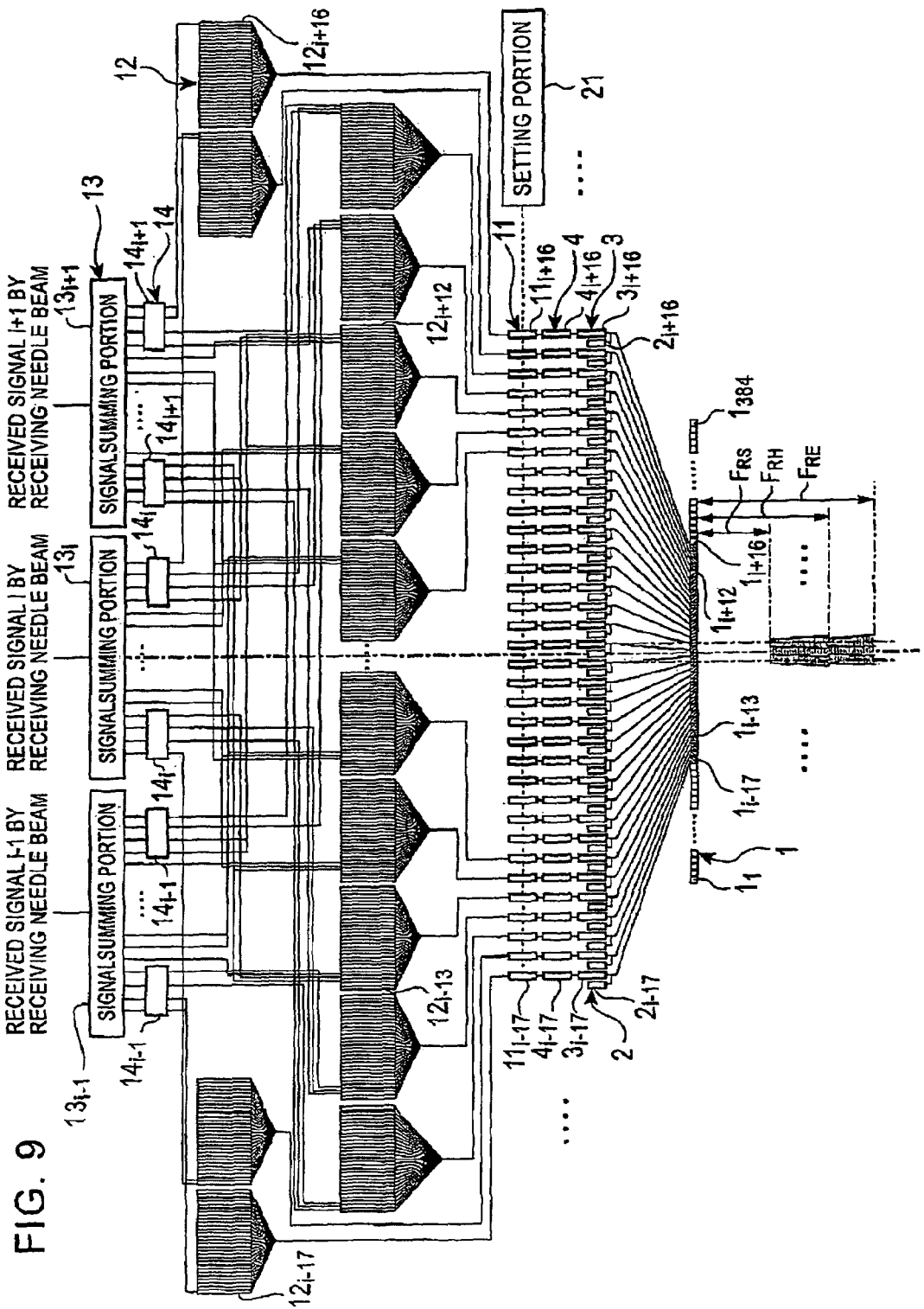
FIG. 9 is a block diagram showing the overall constitution of a third structure, which is a modification of the second structure.

FIG. 9 shows the constitution of a third structure as a modification of the second structure. In the third structure, a receive needle beam is formed using 24 elements when the distance from the transducer array 1 is within a range of $F_{RS}$ to $F_{RH}$, and a receive needle beam is formed using 32 elements when the distance from the transducer array 1 is within a range of $F_{RH}$ to $F_{RE}$. The description of components similar in function to those shown in FIG. 8 will be omitted. In this constitution, a partly clearing portion 14 is newly added. For example, using 24 elements of elements $1_{i-12}$ to $1_{i+11}$, a receive needle beam is formed in a range where the distance from the transducer array 1 is $F_{RS}$ to $F_{RH}$, and using 32 elements of elements $1_{i-16}$ to $1_{i+15}$, a receive needle beam is formed in a range where the distance from the transducer array 1 is $F_{RH}$ to $F_{RE}$. Signals received by elements $1_{i-16}$ to $1_{i-13}$ and elements $1_{i+12}$ to $1_{i+15}$ are not necessary for forming a receive needle beam in the distance range of $F_{RS}$ to $F_{RH}$. The partly clearing portion $14_i$ zero-clears the amplitude of data of signals that are received by elements $1_{i-16}$ to $1_{i-13}$ and elements $1_{i+12}$ to $1_{i+15}$ and time-axis converted and that correspond to the time range used for forming a receive needle beam in the distance range of $F_{RS}$ to $F_{RH}$. Other partly clearing portions $14_{i-1}$ and $14_{i+1}$ have the same function.

In the example shown in FIG. 9, the number of elements used for forming a receive needle beam is changed once according to the distance from the transducer array. However, by slightly changing the above-described constitution, the number of elements used for forming a receive needle beam can be changed more than once.

The above-described constitution in which the number of elements used for forming a receive needle beam is changed once according to the distance from the transducer array is effective in solving the problem in which the beam diameter is large at a large distance when the range where a receive needle beam is formed is lengthened.

Similarly, a constitution in which the number of elements used for forming a receive needle beam is changed more than once according to the distance from the transducer array can be added to the first structure.

Figure 10:
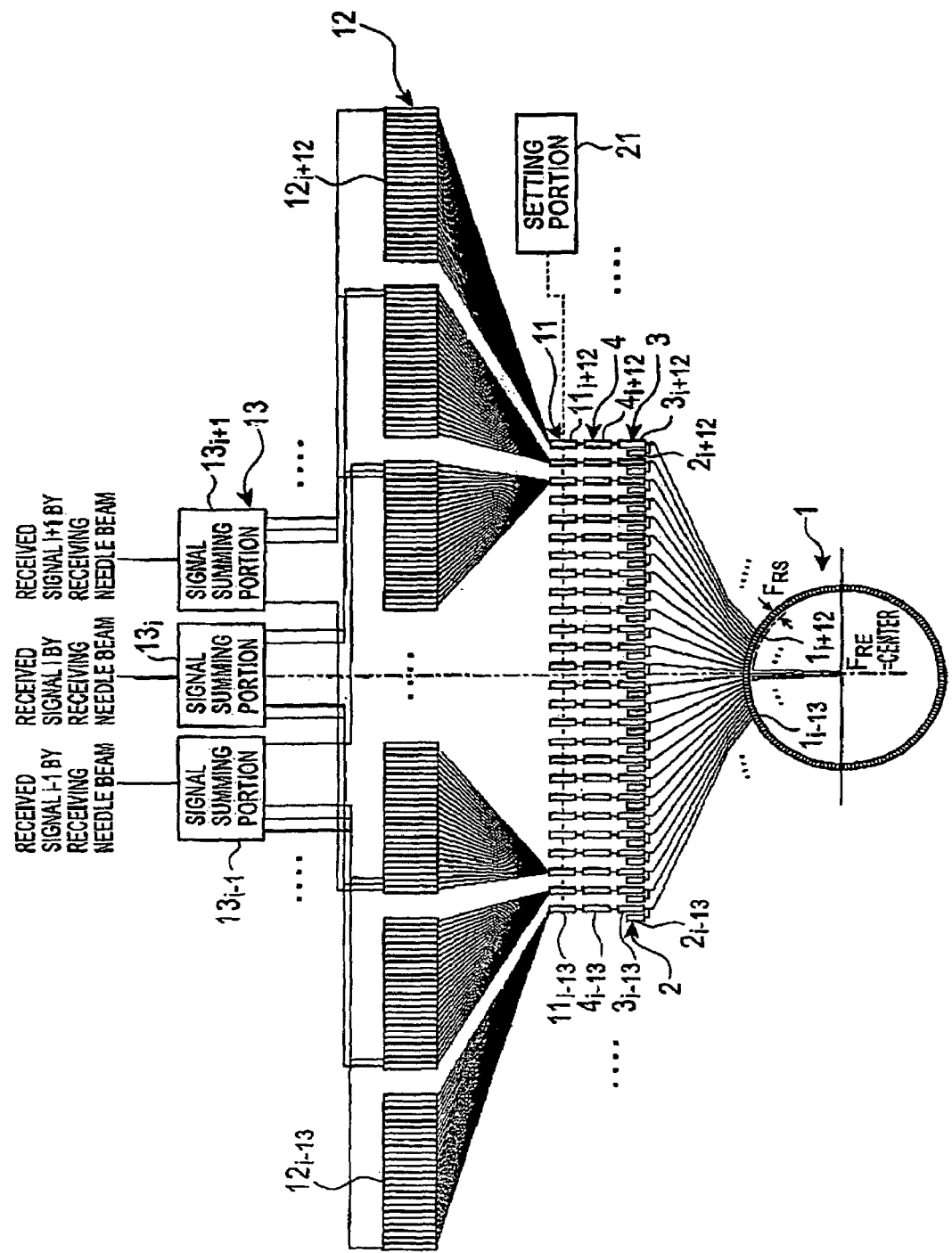
FIG. 10 is a block diagram showing the overall constitution of a fourth structure, which is another modification of the second structure.

Next, FIG. 10 shows the constitution of a fourth structure as another modification of the second structure. In the fourth structure, an annular array (annular transducer array) is used as a transducer array 1. Since an annular transducer array differs from a linear array in geometric shape of transducer array 1, the function expressing the propagation time relationship described with reference to FIGS. 6 and 7 changes. Therefore, the operation of the time axis conversion portion 11 changes. However, since the change is a simple change that can be easily obtained by a geometric calculation by reference to FIGS. 6 and 7, the description thereof will be omitted. The operations of the components other than the time axis conversion portion 11 and the setting portion 21 are exactly the same as those in the case of FIG. 8.

In this way, when an annular transducer array is used, a receive needle beam curtain can be generated in the range where the distance from the transducer array 1 is $F_{RS}$ to $F_{RE}$.

Similarly, an annular transducer array can be used in the first structure. A constitution in which the number of elements used for forming a receive needle beam is changed more than once according to the distance from the transducer array can also be added.

Figure 11:
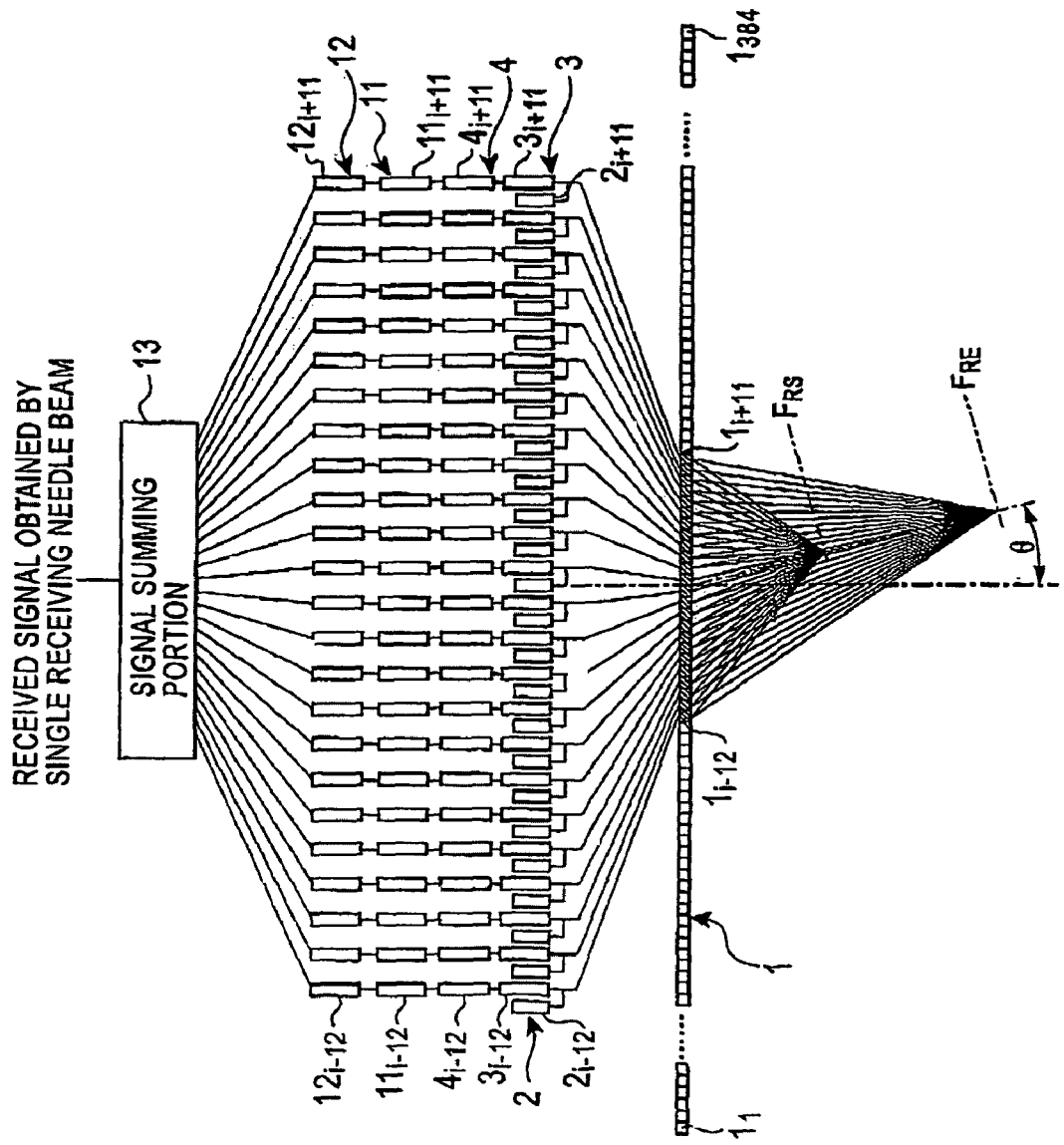
FIG. 11 is a diagram showing a constitution in which a single needle beam is formed in the direction of angle θ.
Figure 13:
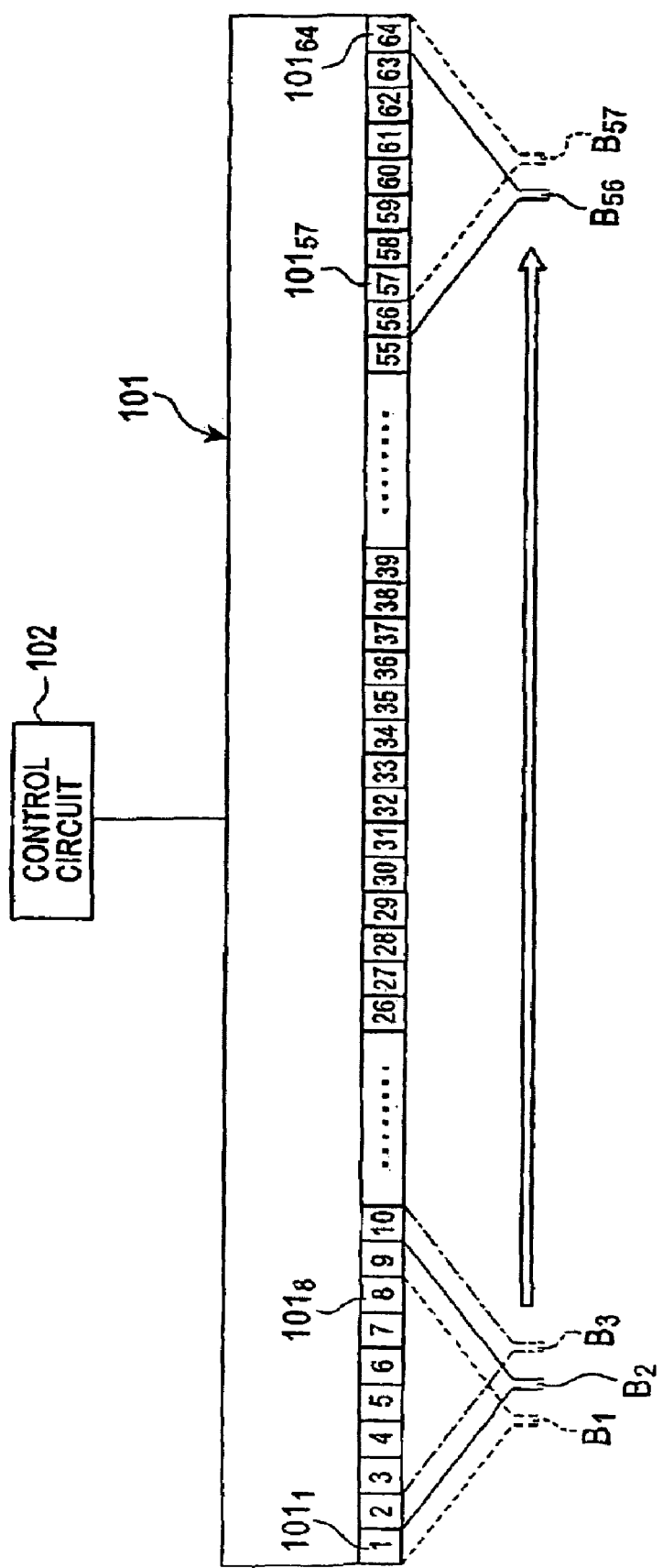
FIG. 13 is a block diagram showing a conventional ultrasonic inspection apparatus.

As still another modification of the second structure, a constitution in which a receive needle beam is formed in a direction inclined at an angle θ to the normal to the transducer array 1 as shown in FIG. 11 is also possible. Also in this case, the time axis conversion portion 11 time-axis converts signals received by elements $1_{i-12}$ to $1_{i+11}$ according to the distance between elements $1_{i-12}$ to $1_{i+11}$ and a continuous line of received-wave focuses formed in the direction of angle θ. For ease of explanation, FIG. 11 shows a constitution in which a single needle beam is formed in the direction of angle θ.

By making the time axis conversion portion 11 perform the same operation as that described above and using the constitution of FIG. 8, a needle beam curtain can be formed in the direction of angle θ. According to the shape and direction of the internal defect to be detected, an angle θ can be selected so that an echo having a sufficient S/N can be obtained.

Similarly, also in the first structure, a receive needle beam can be formed in a direction inclined at an angle θ. A constitution in which the number of elements used for forming a receive needle beam is changed more than once according to the distance from the transducer array can also be added.

Ultrasonic waves can be transmitted from all of the elements of the transducer array 1 at the same time. Alternatively, by controlling the timing when an electric pulse is applied to each element of the transducer array 1 from the pulser 2, ultrasonic waves can be transmitted diagonally to the normal to the transducer array 1, or ultrasonic waves can be transmitted so as to converge under the transducer array. In short, according to the shape of the internal defect to be detected, a method for transmitting waves can be selected so that an echo having a sufficient S/N can be obtained.

Aspects of Japanese Unexamined Patent Application Publication No. 2003-28846 will be again described. In Japanese Unexamined Patent Application Publication No. 2003-28846, signals received by the transducer array is stored in a two-dimensional memory, and by scanning the memory, receive beam focuses are formed throughout a predetermined depth range. In contrast, as described below, we process and store received signals in a memory so as to be used as they are for forming receive beam focuses. Therefore, there is no need to scan the memory, and the processing speed can be, significantly improved.

(1) Just after signals necessary for forming receive beam focuses are A/D converted, they are beforehand extracted or time-axis converted and are then stored in a memory.

(2). Only by addition of signals stored in the memory, a continuous line of receive beam focuses is formed in a desired direction.

In Japanese Unexamined Patent Application Publication No. 2003-28846, by phase-synthesizing all of the n received signals received by n elements, a focus of a receive beam is formed at a specific position. In this case, since a large proportion of the elements do not contribute to formation of the receive beam, calculation in phase synthesis is wasteful, and a noise signal of large amplitude is generated. In our structures, a small group of transducers is selected from the transducer array 1, and a receive beam focus is formed using only this transducer group. Therefore, unlike Japanese Unexamined Patent Application Publication No. 2003-28846, there are no problems of wasteful calculation and generation of a noise signal of large amplitude.

EXAMPLE

FIG. 12 shows the result of detection of minute non-metal inclusions in a thin steel sheet 2 to 3 mm thick performed to verify effectiveness using a transducer array having a frequency of 50 MHz and including 384 elements arranged at 0.1 mm intervals. In this experiment, detection of non-metal inclusions was performed while conveying a steel sheet using a transfer stage. The experiment was performed using the apparatuses of the first and second structures. For contrast, an apparatus capable of realizing the method for forming a received-wave focus shown in Japanese Unexamined Patent Application Publication No. 2003-28846 was also prepared and an experiment was performed. In addition, for contrast with a common electronic scanning technique, using the same transducer array, an experiment using a common linear electronic scanning (converging transmit and receive beams are electronically scanned) was also performed. FIG. 12 shows C-scopes obtained in the experiments. The amplitudes of echo signals from internal defects were detected. According to the amplitudes, luminance modulations were performed to display the images of the internal defects. The horizontal direction of the C-scopes of FIG. 12 is the direction in which the steel sheet was conveyed. In the common linear electronic scanning, the focal length of transmit and receive converging beams was changed a plurality of times (experiments were performed by re-conveying the steel sheet every time the focal length is changed), and there is shown the C-scope in the case where the most clearest internal defect image is obtained (focal length in water: 15 mm). The C-scopes obtained using the apparatus of FIG. 12 and the apparatus of Japanese Unexamined Patent Application Publication No. 2003-28846 are C-scopes obtained in the case where the steel sheet is conveyed at a maximum limit speed at which a C-scope equivalent to the C-scope obtained using the common linear electronic scanning can be obtained. In the case of our apparatus, the internal defect image obtained using the apparatus of the first structure is substantially the same as the internal defect image obtained using the apparatus of the second structure. Therefore, in FIG. 12 are shown C-scopes obtained using the apparatus of the second structure. Table 1 shows the maximum conveying speed and the time required to visualize the region shown in FIG. 12 in the above experiments. However, in the case of the common linear electronic scanning, there are shown the steel sheet conveying maximum speed and the necessary time at a single focal length setting. In the case where the entire cross section of a steel sheet 2 to 3 mm thick is inspected using the common linear electronic scanning, even if only the time required for detection is considered, it requires about 10 times the necessary time of Table 1.

TABLE 1

| Apparatus | Steel sheet conveying maximum speed | Necessary time (s) |
| --- | --- | --- |
| Inventive Apparatus | 1000 mm/s | 0.016 |
| Apparatus of Japanese Unexamined Patent Application Publication No: 2003-28846 | 100 mm/s | 0.16 |
| Common linear electronic scanning apparatus | 10 mm/s | 1.6 (Necessary time at a single focal length setting) |

The C-scopes of FIG. 12 and Table 1 show that, in the case of our apparatus, even if the steel sheet is conveyed at 10 to 100 times the speed as in the cases of conventional apparatuses (the apparatus of Japanese Unexamined Patent Application Publication No. 2003-28846 and the common linear electronic scanning apparatus), almost the same internal defect image can be obtained. In the apparatus of Japanese Unexamined Patent Application Publication No. 2003-28846, all of the n received signals received by n elements are phase-synthesized, and therefore a large proportion of the transducers do not contribute to formation of a receive beam. Therefore, due to the cyclic noise included in signals received by the transducers that do not contribute to formation of a receive beam, the noise level is high throughout the C-scope. FIG. 12 clearly shows the problematic point of the apparatus of Japanese Unexamined Patent Application Publication No. 2003-28846. In addition, the repetition of transmitting and receiving of ultrasonic waves in our apparatus is 10 kHz, whereas the repetition of transmitting and receiving of ultrasonic waves in the apparatus of Japanese Unexamined Patent Application Publication No. 2003-28846 is 1 kHz at the highest as shown in Japanese Unexamined Patent Application Publication No. 2003-28846. Our apparatuses can be advantageously applied to inspection of a test object being conveyed at a high speed, or inspection of a test object performed by scanning a transducer array at a high speed.

The apparatuses of the first and second structures transmit and receive ultrasonic waves from all of the elements $1_1$ to $1_{384}$ of the transducer array 1. However, ultrasonic waves may be transmitted and received using some of the elements. The total number of elements is not limited to 384.

INDUSTRIAL APPLICABILITY

Our methods include the steps of transmitting ultrasonic waves from some or all of the ultrasonic transducers of the transducer array, receiving reflected waves generated by the transmitted ultrasonic waves using some or all of the ultrasonic transducers of the transducer array, converting the received signals into digital waveform signals, converting the time axis of the digitalized received signal of each transducer on the basis of the distance between each transducer of at least one ultrasonic transducer group consisting of a plurality of ultrasonic transducers selected from the transducer array and a continuous line of received-wave focuses formed inside the test object, and additively synthesizing the time-axis converted received signals of each transducer. Therefore, a receive needle beam including a continuous or semi-continuous line of receive beam focuses can be formed under the transducer array. In addition, since the at least one ultrasonic transducer group consisting of a plurality of ultrasonic transducers includes a plurality of groups, and additive synthesis are performed in the plurality of ultrasonic transducer groups at the same time, a curtain of closely-arranged receive needle beams can be formed under the transducer array. Therefore, inspection omission accompanying linear electronic scanning does not occur during inspection of an object moving at a high speed, or during inspection performed by moving a transducer array at a high speed. Therefore, there is a non-conventional advantage of being able to inspect the entire volume of an object relatively moving at a high speed.

What is claimed is:

1. An ultrasonic cross-sectional inspection method for inspecting a cross section of a test object using a transducer array comprised of a plurality of ultrasonic transducers arranged substantially in one dimension, the method comprising the steps of:

transmitting ultrasonic waves from some or all of the ultrasonic transducers in the transducer array;

receiving reflected waves generated by the transmitted ultrasonic waves using some or all of the ultrasonic transducers in the transducer array;

converting the received signals into digital waveform signals;

transforming the timing between the digitalized signal data received by each transducer element in at least one transducer group, which is comprised of a plurality of transducer elements selected from the transducer array, on the basis of the distances between the transducer element and spatially continuous focuses of receiving beam set to be formed in the test object;

summing the timing-transformed signals received by transducer elements in the transducer group; and wherein plural transducer groups comprised of the plurality of transducer elements are selected from the transducer array, and summing is carried out for the plural ultrasonic transducer groups in parallel.

2. The cross-sectional inspection method according to claim 1, wherein the number of ultrasonic transducer elements constituting each ultrasonic transducer group is changed according to the distance between the transducer array and the focus.

3. An ultrasonic cross-sectional inspection method for inspecting a cross section of a test object using a transducer array comprised of a plurality of ultrasonic transducers arranged substantially in one dimension, the method comprising the steps of:

- transmitting ultrasonic waves from some or all of the ultrasonic transducers in the transducer array;
- receiving reflected waves generated by the transmitted ultrasonic waves using some or all of the ultrasonic transducers in the transducer array;
- converting the received signals into digital waveform signals;
- extracting, on the basis of the distance between each transducer element in at least one ultrasonic transducer group composed of a plurality of ultrasonic transducer elements selected from the transducer array and n (n≧2) focuses of receiving beam set to be formed in the test object, signals contributing to formation of each of the n focuses from the digitalized received signals by each transducer element; and
- summing the signals extracted for each of the n focuses.

4. The cross-sectional inspection method according to claim 3, wherein plural ultrasonic transducer groups comprised of the plurality of ultrasonic transducer elements are selected from the transducer array, and summing is performed in the ultrasonic transducer groups in parallel.

5. The cross-sectional inspection method according to claim 4, wherein the number of ultrasonic transducer elements constituting each ultrasonic transducer group is changed according to the distance between the transducer array and the focus.

6. The cross-sectional inspection method according to claim 4, wherein the distances between the n (n≧2) focuses of receiving beam set to be formed in the test object is changed according to the distance between the transducer array and the focuses.

7. The cross-sectional inspection method according to claim 3, wherein the number of ultrasonic transducer elements constituting each ultrasonic transducer group is changed according to the distance between the transducer array and the focus.

8. The cross-sectional inspection method according to claim 7, wherein the distances between the n (n≧2) focuses of receiving beam set to be formed in the test object is changed according to the distance between the transducer array and the focuses.

9. The cross-sectional inspection method according to claim 3, wherein the distances between the n (n≧2) focuses of receiving beam set to be formed in the test object is changed according to the distance between the transducer array and the focuses.

10. An ultrasonic cross-sectional inspection apparatus for inspecting a cross section of a test object using a transducer array comprised of a plurality of ultrasonic transducers arranged substantially in one dimension, the apparatus comprising:

- means for transmitting ultrasonic waves from some or all of the ultrasonic transducers in the transducer array;
- means for receiving reflected waves generated by the transmitted ultrasonic waves using some or all of the ultrasonic transducers in the transducer array;
- means for converting the received signals into digital waveform signals;
- means for extracting, on the basis of the distance between each transducer element in at least one ultrasonic transducer group comprised of a plurality of ultrasonic transducers selected from the transducer array and n (n≧2) focuses of receiving beam set to be formed in the test object, signals contributing to formation of each of the n focuses from the digitalized received signals by each transducer element; and
- means for summing the signals extracted for each of the n focuses.

11. The cross-sectional inspection apparatus according to claim 10, wherein the means for summing carries out summing for the plural ultrasonic transducer groups in parallel.

* * * * *